(12) United States Patent
Palmas et al.

(10) Patent No.: US 7,622,625 B2
(45) Date of Patent: Nov. 24, 2009

(54) PURGE GAS STREAMS TO STAGNANT ZONES WITHIN OXYGENATE-TO-OLEFIN REACTOR

(75) Inventors: Paolo Palmas, Des Plaines, IL (US); Daniel N. Myers, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 508 days.

(21) Appl. No.: 11/235,974

(22) Filed: Sep. 27, 2005

(65) Prior Publication Data

US 2006/0094915 A1 May 4, 2006

Related U.S. Application Data

(60) Provisional application No. 60/624,035, filed on Nov. 1, 2004.

(51) Int. Cl.
 *C07C 1/00* (2006.01)
(52) U.S. Cl. ..................... 585/640; 585/639
(58) Field of Classification Search ......... 585/638–640; 422/139–145, 147
See application file for complete search history.

(56) References Cited

U.S. PATENT DOCUMENTS

| | | | |
|---|---|---|---|
| 4,440,871 A | 4/1984 | Lok et al. | 502/214 |
| 5,095,163 A | 3/1992 | Barger | 585/640 |
| 5,126,308 A | 6/1992 | Barger et al. | 502/214 |
| 5,191,141 A | 3/1993 | Barger et al. | 585/640 |
| 5,744,680 A | 4/1998 | Mulvaney, III et al. | 585/640 |
| 6,051,746 A * | 4/2000 | Sun et al. | 585/639 |
| 6,166,282 A | 12/2000 | Miller | 585/638 |
| 6,403,854 B1 | 6/2002 | Miller et al. | 585/638 |
| 6,459,009 B1 | 10/2002 | Miller et al. | 585/809 |

* cited by examiner

*Primary Examiner*—In Suk Bullock
(74) *Attorney, Agent, or Firm*—Mark Goldberg

(57) ABSTRACT

The present invention comprises a process for conversion of oxygenates to olefins comprising contacting within a reactor the oxygenates with a catalyst to produce light olefins and wherein the reactor comprises at least two zones, a first zone wherein gas circulates at a faster rate than a second zone wherein a gas circulates at a slower rate; and inserting a quantity of inert gas into the second zone to increase circulation of any materials located in said second zone. The invention prevents accumulation of undesirable by-products within stagnant zones within the reactor and reduces the amount of coke deposited on catalyst or on surfaces within these zones.

5 Claims, 2 Drawing Sheets

PURGE GAS STREAMS TO STAGNANT ZONES WITHIN OXYGENATE-TO-OLEFIN REACTOR

CROSS-REFERENCE TO RELATED APPLICATION

This application claims priority from Provisional Application Ser. No. 60/624,035 filed Nov. 1, 2004, the contents of which are hereby incorporated by reference.

FIELD OF INVENTION

The present invention relates generally to a method to prevent coke buildup in an Oxygenate-To-Olefin (OTO) Process. More particularly, the present invention relates to the use of a purge stream of inert gas to prevent buildup of undesirable by-products, including coke, in stagnant zones within the reactor.

BACKGROUND OF INVENTION

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the steam cracking of petroleum feeds. The art has long sought a source other than petroleum for the massive quantities of raw materials that are needed to supply the demand for these light olefin materials. A great deal of the prior art's attention has been focused on the possibility of using hydrocarbon oxygenates and more specifically methanol as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol and other oxygenates from these types of raw materials is well established.

The art has focused on different procedures for catalytically converting oxygenates such as methanol into the desired light olefin products. These light olefin products must be available in quantities and purities such that they are interchangeable in downstream processing with the materials that are presently produced using petroleum sources. Although many oxygenates have been discussed in the prior art, the principal focus has been on methanol conversion technology. There are two major techniques for conversion of methanol to light olefins. The first of these MTO processes is based on early German and American work with a catalytic conversion zone containing a zeolitic type of catalyst system. U.S. Pat. No. 4,387,263 reports on a series of experiments with methanol conversion techniques using a ZSM-5-type of catalyst system wherein the problem of DME recycle is a major focus of the technology disclosed. Although good yields of ethylene and propylene were reported in this '263 patent, unfortunately they were accompanied by substantial formation of higher aliphatic and aromatic hydrocarbons which the patentees speculated might be useful as an engine fuel and specifically as a gasoline-type of material.

This early MTO work with a zeolitic catalyst system was then followed up by the Mobil Oil Company who also investigated the use of a zeolitic catalyst system like ZSM-5 for purposes of making light olefins.

Primarily because of an inability of this zeolitic MTO route to control the amounts of undesired $C_4^+$ hydrocarbon products produced by the ZSM-5 type of catalyst system, the art soon developed a second MTO conversion technology based on the use of a non-zeolitic molecular sieve catalytic material. This branch of the MTO art is perhaps best illustrated by reference to UOP's extensive work in this area as reported in numerous patents of which U.S. Pat. Nos. 5,095,163; 5,126,308 and 5,191,141 are representative. This second approach to MTO conversion technology was primarily based on using a catalyst system comprising a non-zeolitic molecular sieve, generally a metal aluminophosphate (ELAPO) and more specifically a silicoaluminophosphate molecular sieve (SAPO), with a strong preference for a SAPO species that is known as SAPO-34. This SAPO-34 material was found to have a very high selectivity for light olefins with a methanol feedstock and consequently very low selectivity for the undesired corresponding light paraffins and the heavier materials. This ELAPO catalyzed MTO approach is known to have at least the following advantages relative to the zeolitic catalyst route to light olefins: (1) greater yields of light olefins at equal quantities of methanol converted; (2) capability of direct recovery of polymer grade ethylene and propylene without the necessity of the use of extraordinary physical separation steps to separate ethylene and propylene from their corresponding paraffin analogs; (3) sharply limited production of by-products such as stabilized gasoline; (4) flexibility to adjust the product ethylene-to-propylene weight ratios over the range of 1.5:1 to 0.75:1 by minimal adjustment of the MTO conversion conditions; and (5) significantly less coke make in the MTO conversion zone relative to that experienced with the zeolitic catalyst system.

For various reasons well articulated in UOP's patents, U.S. Pat. Nos. 6,403,854; 6,166,282 and 5,744,680 (all of the teaching of which are hereby specifically incorporated by reference) the consensus of the practitioners in this OTO or MTO art points to the use of a fluidized reaction zone along with a fluidized regeneration zone as the preferred commercial solution to the problem of effectively and efficiently using an ELAPO or SAPO-type of catalyst system. As is well-understood by those of skill in the fluidization art, the use of this technology gives rise to a substantial problem of solid-vapor separation in order to efficiently separate the particles of the fluidized catalyst from the vapor products of the OTO or MTO reaction as well as from any unreacted oxygenate materials exiting the OTO or MTO conversion zone. Standard industry practice for accomplishing this difficult separation step involves its use of one or more vapor-solid cyclonic separating means which are well illustrated in the sole drawing of U.S. Pat. No. 6,166,282 where a series of three cyclonic separation means are used to separate spent OTO or MTO catalyst from the product effluent stream.

Despite the promising developments associated with the ELAPO or SAPO catalyzed routes to light olefins there are still substantial hurdles to overcome. Coking of surfaces within the reactor can reduce yield and productivity of these processes. Two particular potential coking problems are discussed herein. A coking problem that is the subject of this invention to resolve is the coking of surfaces as the result of reactive materials remaining in stagnant zones within the reactor. A second coking problem can be the result of recycling of unreacted oxygenate together with recycling of various reaction by-products combined with the oxygenate feed stream.

SUMMARY OF THE INVENTION

The present invention comprises a process for conversion of oxygenates to olefins comprising contacting within a reactor the oxygenates with a catalyst to produce light olefins and wherein the reactor comprises at least two zones, a first zone wherein gas travels at a faster rate than a second zone wherein a gas travels at a slower rate and has some potential stagnant zones; and inserting a quantity of inert gas into the second zone to increase circulation of any materials located in said second zone. The invention prevents accumulation of undesirable by-products within stagnant zones within the reactor and reduces the amount of coke deposited on catalyst within the stagnant zones or upon surfaces within these zones.

Other objects, embodiments, advantages and features of the present invention will be clear to someone of ordinary skill in the chemical engineering art from a detailed examination of the following description of the invention as well as the attached drawings.

TERMS AND CONDITIONS DEFINITIONS

Figure 1:
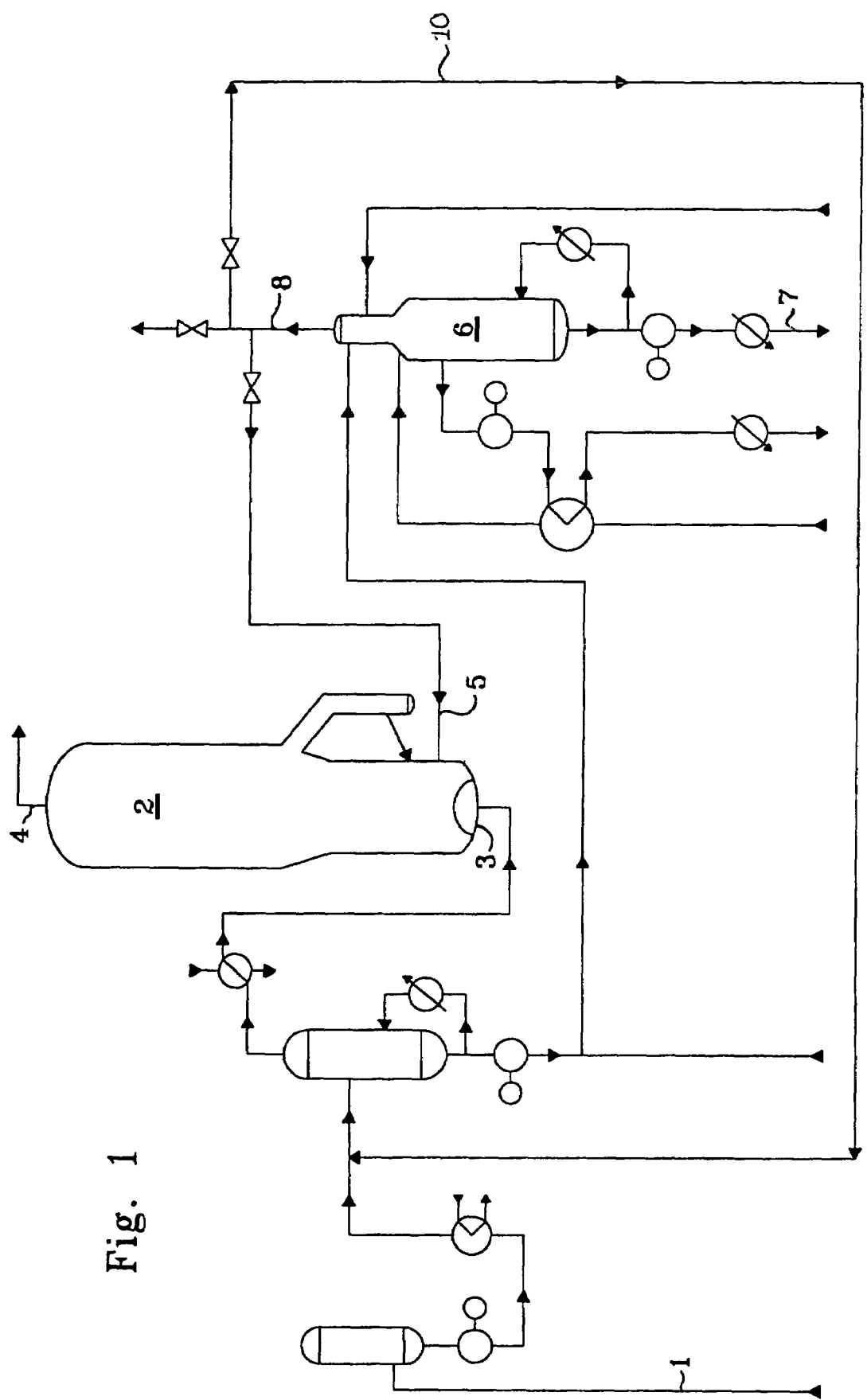
FIG. 1 is a process flow diagram showing the reactor with separate injection of recycled oxygenate from the main feed stream.

The following terms and conditions are used in the present specification with the following meanings: (1) a "portion" of a stream means either an aliquot part that has the same composition as the whole stream or a part that is obtained by eliminating a readily separable component therefrom (e.g. if the stream contains hydrocarbons in admixture with steam, then after condensation of a major portion of the steam, it comprises an aqueous portion and a hydrocarbon portion). (2) an "overhead" stream means the net overhead recovered from the specified zone after recycle of any portion to the zone for reflux or any other reason. (3) a "bottom" stream means the net bottom stream from the specified zone obtained after recycle of any portion for purposes of reheating and/or reboiling and/or after any phase separation. (4) a line is "blocked-off" when it contains a valve that is set to a position that prevents flow through the line. (5) presence of necessary compressors and/or pumps is understood when flow is shown from a zone of relatively low pressure to a zone of higher pressure. (6) presence of necessary heating and/or cooling means is implied when flow is shown between zones operating at different temperatures. (7) an ingredient is "lifted" or "stripped" when it is concentrated in the overhead stream withdrawn from the specified zone. (8) a "vapor" stream means a stream containing one or more components in the gaseous state. (9) the term "light olefins" means ethylene, propylene and mixtures thereof. (10) The expression "ELAPO" molecular sieve means a material having a three-dimensional microporous framework structure of $ALO_2$, $PO_2$ and $ELO_2$ tetrahedral units having the empirical formula:

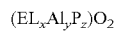

where EL is a metal selected from the group consisting of silicon, magnesium, zinc, iron, cobalt, nickel, manganese, chromium and mixtures thereof, x is the mole fraction of EL and is at least 0.005, y is the mole fraction of Al and is at least 0.01 z is the mole fraction of P and is at least 0.01 and x+y+z=1. When EL is a mixture of metals, x represents the total amount of the metal mixture present. Preferred metals (EL) are silicon, magnesium and cobalt with silicon being especially preferred. (11) The expression "SAPO molecular sieve" means an ELAPO molecular sieve wherein the EL element is silicon as described in U.S. Pat. No. 4,440,871. (12) The expression "OTO" process means a process for converting an oxygenate to light olefins and in a preferred embodiment when the oxygenate is methanol the OTO process is referred to as an MTO process herein. (13) The term "oxygenate" means an oxygen-substituted aliphatic hydrocarbon preferably containing 1 to 10 carbon atoms. (14) A reagent is "compatible" with a catalyst system when the physical, chemical and catalytic properties of the catalyst are not permanently altered by interaction with the reagent.

DETAILED DESCRIPTION OF THE INVENTION

In the instant OTO process the feed stream comprises one or more oxygenates. The term "oxygenate" is employed herein to include alcohols, ethers, and carbonyl compounds (e.g. aldehydes, ketones, carboxylic acids, and the like). The oxygenate feedstock preferably contains at least one oxygen atom and about 1 to 10 carbon atoms and, and preferably, contains from about 1 to 4 carbon atoms. Suitable oxygenates include lower straight or branched chain alkanols, and their unsaturated counterparts. Representatives of suitable oxygenate compounds include methanol, dimethyl ether (DME), ethanol, diethyl ether, methylether, formaldehyde, dimethyl ketone, acetic acid, and mixtures thereof.

In the OTO conversion step of the present invention, the oxygenate feedstock is catalytically converted to hydrocarbons containing aliphatic moieties such as—but not limited to—methane, ethane, ethylene, propane, propylene, butylene, and limited amounts of other higher aliphatics by contacting the feedstock with a an ELAPO-containing catalyst. A diluent is not required but is a useful option to maintain the selectivity of the catalyst to produce light olefins, particularly ethylene and propylene. The phase change between steam and liquid water can also be employed to advantage in transferring heat between the feedstock and the reactor effluent, and the separation of the steam diluent from the product requires simple condensation of the water to separate the water from the hydrocarbons. Ratios of 1 mole of oxygenates to about 0.1 to 5 moles of diluent have been disclosed as being useful in the OTO conversion reaction. The preferred diluent is steam.

The oxygenate conversion step of the present invention is preferably conducted such that the oxygenate feedstock is contacted in a vapor phase in a reaction zone with a ELAPO molecular sieve catalyst at effective conversion conditions to produce olefinic hydrocarbons, i.e., an effective temperature, pressure, weight hourly space velocity (WHSV). The OTO step is affected for a period of time sufficient to produce the desired light olefin products. The oxygenate conversion step is effectively carried out over a wide range of pressures, including autogenous pressures. At pressures between about 0.1 atmospheres (10.1 kPa) and about 100 atmospheres (10.1 MPa), the formation of light olefin products will be affected although the optimum amount of product will not necessarily form at all pressures. The pressure will more preferably range from about 1 to about 10 atmospheres (101.3 to 1013.3 kPa). The pressures referred to herein are exclusive of any diluent and refer to the partial pressure of the oxygenate feedstock.

The temperature which may be employed in the oxygenate conversion step may vary over a wide range depending, at least in part, on the selected ELAPO molecular sieve catalyst. In general, the OTO step can be conducted at an effective temperature between about 350° and about 600° C.

In the oxygenate conversion step of the present invention, it is preferred that the ELAPO catalysts have relatively small pores. Preferably, the small pore catalysts have a substantially uniform pore structure, e.g., substantially uniformly sized and shaped pore with an effective diameter of less than about 5 angstroms. Suitable catalyst may comprise an ELAPO molecular sieve and a matrix material. A preferred ELAPO molecular sieve is one in which the element (EL) content varies from about 0.005 to about 0.2 mole fraction and in which EL is silicon (usually referred to as SAPO). The SAPOs which can be used in the instant invention are preferably any of those described in U.S. Pat. Nos. 4,440,871; 5,126,308 and 5,191,141 (all of which are hereby specifically incorporated by reference). Especially preferred SAPOs include the SAPO-34 and SAPO-17 structures with SAPO-34 being most preferred.

The ELAPO catalyst is preferably incorporated into solid particles containing one or more matrix materials in which the catalyst is present in an amount effective to promote the desired oxygenate conversion reactions. In one aspect, the solid particles comprise a catalytically effective amount of the catalyst and at least one matrix material, preferably selected from the group consisting of binder materials, filler materials, and mixtures thereof in an amount selected to provide desired properties, e.g., desired catalyst dilution, mechanical strength, and the like to the solid particles. The preparation of solid particles comprising ELAPO catalyst and matrix materials in a fluidized size range is conventional and well known in the spray drying art and, therefore, need not be discussed in detail herein.

During the oxygenate conversion reactions, a carbonaceous material, i.e., coke, is deposited on the catalyst in an amount of about 1 to 20 mass-% and more commonly about 1.5 to 9 mass-%. The carbonaceous deposit material has the effect of reducing the number of available active sites on the catalyst which thereby affects the extent of the conversion. During the OTO conversion step a portion of the coked catalyst is withdrawn from the OTO reaction zone and passed to a regeneration step where it is regenerated with an oxygen-containing medium (e.g. air) to remove at least a portion of the carbonaceous material and returned to the oxygenate conversion reaction zone.

The problem of recovery of ELAPO catalyst particles from the product effluent stream withdrawn from the OTO conversion zone is a problem that is unique to a fluidized bed type of system. In a fluidized system large amounts of finely divided catalyst particles are continuously transported between a reaction zone and a regeneration zone and in the OTO reaction zone they are admixed with the oxygenate feed stream in an amount which is conveniently measured in terms of a WHSV calculated on the basis of mass hourly flow rate of the sum of the mass of oxygenate reactants passed to the MTO conversion zone plus any other oxygenate or hydrocarbon reactants present in the feed or recycle streams divided by the mass of the ELAPO catalyst present in the OTO conversion zone. WHSV for use in the fluidized in the OTO conversion zone associated with the present invention can range from about 0.1 to about 100 $hr^{-1}$ with best results obtained within the range of about 0.5 to 40 $hr^{-1}$.

It has been found advantageous to have a single stage of cyclones within the reactor vessel and a separate single stage of cyclones downstream of the reactor to capture catalyst during upsets. A separate vessel, referred to herein as a reactor surge vessel is provided downstream of the reactor. A product effluent stream that contains catalyst particles is sent outside of the reactor vessel to the reactor surge vessel. Within the reactor surge vessel are single stage cyclones for separation of the catalyst particles from the effluent. The reactor effluent is sent out the top of the cyclone and then out the top of the reactor surge vessel for further processing. The catalyst that has been removed by use of these cyclones can now be recycled to the main reactor. If desired, the catalyst can be held in a catalyst hopper for return to the reactor as necessary. In addition to the removal of the catalyst by the cyclones, some of the catalyst particles will drop out of the effluent gas within the reactor surge vessel before entering the cyclones. Among the advantages of having the second stage of cyclones separated from the first stage cyclones in the reactor, the diplegs of the second stage cyclones have less pressure drop to overcome than if they would be in immediate series within the same reactor vessel. In addition, having the second stage of cyclones outside of the reactor allows for the product throughput to be increased within the reactor since throughput is limited by vessel size and the process is operated at maximum capacity.

The present invention will be further described in reference to an MTO embodiment using a preferred SAPO-34 catalyst system that has been established to have great utility. The application of the present invention to other oxygenates and to other types of ELAPO catalysts is readily within the competence of someone of ordinary skill in the chemical engineering art.

The starting point for the present invention in an MTO embodiment is a MTO conversion step which utilizes methanol as the principal source of the oxygenate reactant. As indicated above, the preferred ELAPO molecular sieve is a silicoaluminophosphate SAPO system, which has been established as occurring in numerous specific crystal structures. The most preferred SAPO structure for MTO conversion is a SAPO-34 structure. The SAPO-34 molecular sieve can be used alone or may be mixed with a binder and/or filler and formed into shapes such as extrudates, pills, spheres, and the like. A preferred method of forming is to spray dry an aqueous slurry of SAPO-34 powder and filler and/or binder. Any of the inorganic oxides well known in the art may be used as a binder and/or filler such as alumina, silica, alumina-phosphate, silica-alumina, and/or one of the various silica-rich clays such as a kaolin clay that are well known to those of ordinary skill in the art. It is to be understood that the active ingredient is the SAPO-34 molecular sieve and the binder and/or filler is a porous material that is used to provide structural integrity to the catalyst particles. A SAPO-34 catalyst system is ordinarily used in an MTO embodiment in a particle size suitable for a fluidized reactor system—typically an average particle size of 65 to 85 microns.

The fluidized MTO reaction zone using a SAPO-34 catalyst is operated at conditions, which include a temperature of about 350° to 600° C. (662° to 1112° F.) with the preferred range being about 450° to 550° C. (842° to 1022° F.). The pressure used in the MTO conversion step is typically in the range of about 138 to 1000 kPa (20 to 145 psia) and preferably from about 170 to 345 kPa (24.7 to 50 psia). Since the MTO conversion reaction is strongly exothermic, a significant temperature increase will occur across the MTO reaction zone ordinarily of the magnitude of about 100° to 400° C. (180° to 720° F.). In a fluidized MTO reactor system, an external catalyst circulation rate between the reactor and the regenerator will be set at a minimum level desired to hold average coke on the total circulating inventory of the preferred SAPO-34 catalyst entering the MTO conversion zone in a range of about 1 to 20 mass-% of the active SAPO-34 ingredient in the catalyst and, more preferably, in the range of about 1.5 to 9 mass-%.

The regeneration step associated with the MTO conversion step as explained previously will ordinarily use one of the established oxidative techniques for removing the necessary amount of coke from the catalyst prior to recirculation to the conversion zone. The primary factor that will establish the circulation rate between the conversion zone and the regeneration zone is the equilibrium value of coke on catalyst that it is desired to maintain in order to obtain the desired conversion level. SAPO-34 based catalyst systems run quite successfully at conversion levels of 95% or higher and result in a coke made of about 0.6 to 10.4 mass-% of methanol equivalent and more typically 2 to 5 mass-% of methanol equivalent. Knowing the coking rate, one of ordinary skill in the art can then establish a circulation rate to the regenerator based on burning coke at a rate which holds the overall average coke level on the total circulating catalyst inventory used in the MTO conversion zone in the desired range specified hereinbefore. In comparison with traditional hydrocarbon FCC operation, the circulation rate for an MTO fluidized conversion zone will be quite low since the hot regenerated catalyst is not needed to supply heat to the MTO reaction zone.

In the practice of the present invention, there is a production separation section of the apparatus. Reference is made to U.S. Pat. No. 6,459,009, incorporated herein in its entirety. Conventional separation vessels are provided including a demethanizer section for removal of methane, depropanizer section for removal of propane, deethanizer for removal of ethane and oxygenate stripper for removal of unreacted oxygenate. The unreacted oxygenate may be returned to the MTO reaction zone to increase the efficiency of the reaction. In the past, the unreacted oxygenate as simply been returned to the feed stream. However, due to impurities such as di-olefins within the recovered unreacted oxygenate stream, it has been found that the feed distribution grid to the reaction zone may collect coke deposits that eventually interfere with the flow of the feed stream through this distribution grid. These di-olefins and other reactive recycle materials may polymerize and even form undesirable coke deposits. The distribution grid is located at the bottom of the reactor and serves to disperse the feed stream into the MTO reaction zone. It has been found advantageous to send the recovered unreacted oxygenate stream, directly to the reaction zone through nozzle inlets or injection tubes that are provided for that purpose. The use of the separate nozzle inlets or injection tubes provides for simplified cleaning in the event that coke deposits interfere with the gas flow. A high pressure steam or other gas may be introduced into the nozzle inlets for this purpose and may be accomplished with the reactor continuing to operate during the process. It has been found considerably simpler to clean these nozzle inlets instead of shutting down the reactor and cleaning the much more complex feed distribution grid. In the preferred embodiment of the invention, the individual nozzles have extensions that extend into the fluidized catalyst bed. External valving is provided to allow cleaning through any means known to one skilled in the art, such as blasting or reaming of the nozzle extensions in the event that they should be become clogged.

The present invention reduces undesirable coking of the catalyst which is otherwise caused by by-products being formed from gases remaining for additional time in stagnant areas. An inert purge gas is introduced through an inlet or port into sections of the reactor that tend to have stagnant gas. This inert gas may be nitrogen, or preferably is the methane waste product of the demethanizer which removes methane from the product effluent. This methane waste product will also contain hydrogen. The inert purge gas is introduced at sufficient pressure to keep the stagnant areas purged of reaction products. The purge gas produces velocities of about 4% of the rate of the vapors in the main part of the reactor. The resulting mixing of the gases reduces coke formation on the catalyst and surfaces of the reactor. The overall yield of light olefin product can be improved by 1-2% by this process.

DETAILED DESCRIPTION OF THE DRAWINGS

The following description of the present process is made with reference to the attached drawings. In the interest of simplifying the description of the invention in order to facilitate understanding, the drawings do not contain representations of heaters, heat exchangers, coolers, valves, control means and other conventional items that are well known to those of ordinary skill in the chemical engineering art except where their presence is essential to understanding the present invention.

The attached drawings illustrate the instant invention with components numbered as necessary to understand the invention. In FIG. 1 is shown a feed stream 1 that passes through several vessels and lines and is heated and sent to a distribution zone 3 of a reactor 2. Shown as relevant to the present invention, is a product gas stream 4 exiting the top of reactor 2 to be sent to a product separation zone (not shown). A recycle stream of oxygenates and by-products in line 5 is shown entering reactor 2 separate from feed stream 1. This recycle stream of oxygenates and by-products in line 5 is separated from a product stream 10 in an oxygenate stripper 6.

Oxygenate stripper 6 operates to strip any unreacted oxygenates such as methanol, DME and diolefins from the aqueous streams charged thereto and to produce a relatively pure water stream which is withdrawn from the bottom of the stripping zone via a line 7 and is available for further use in the process if for example it is desired to use an aqueous diluent in the operation of the reaction zone within reactor 2. Such diolefins, even in trace amounts, have been found to be the cause of significant degrees of undesired polymerization and fouling. Oxygenate stripper 6 is operated at oxygenate stripping conditions effective to produce an overhead vapor stream which exits oxygenate stripper 6 via a line 8 and comprises a significant portion of the net unreacted oxygenates recovered from the effluent stream and it can be recycled via line 5 which enters reactor 2 through nozzles or injection tubes that are about 3 to 6 cm in diameter in order to enhance the conversion of oxygenates without fouling of the feed distributor from diolefin polymerization and fouling.

Figure 2:
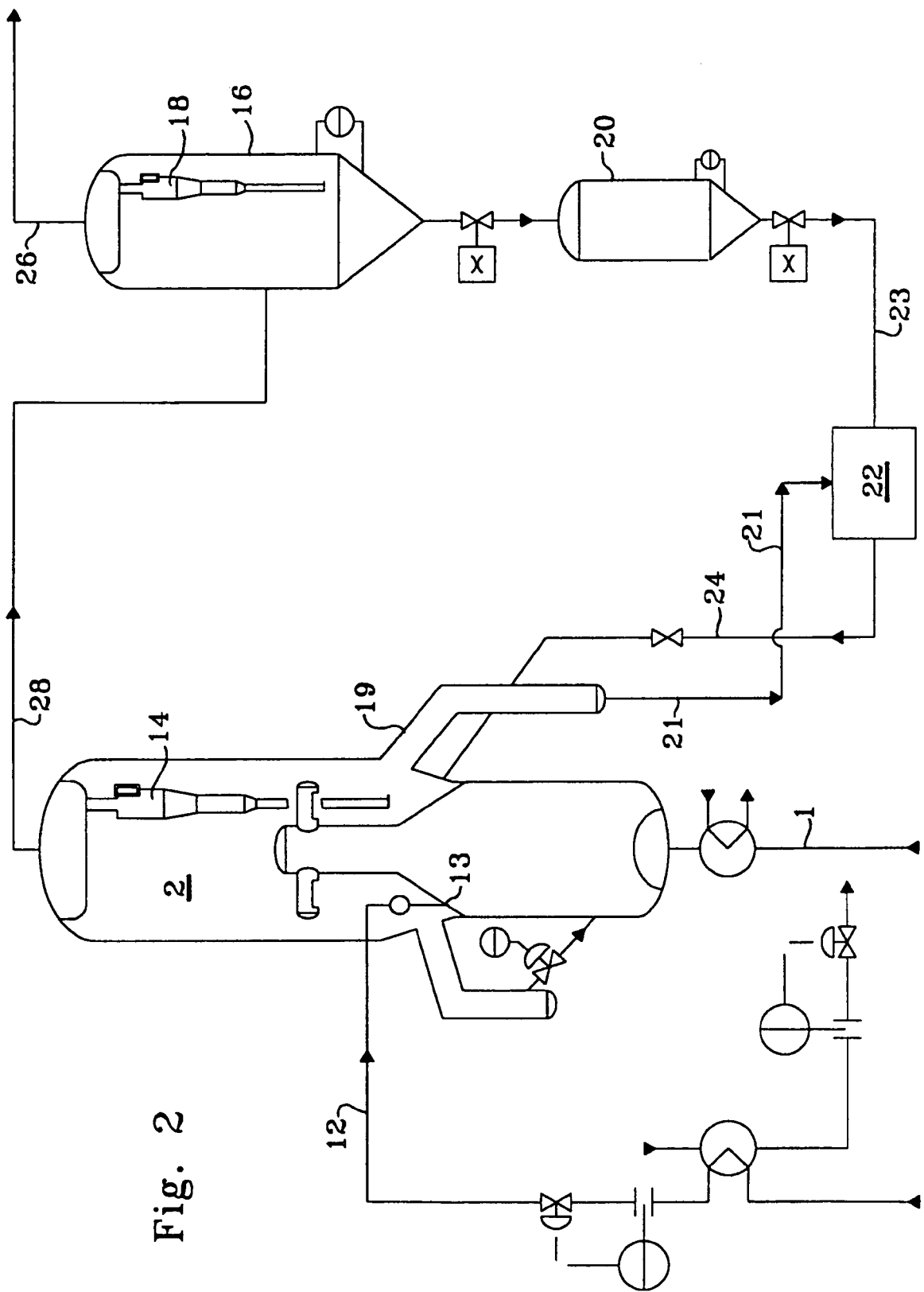
FIG. 2 is a process flow diagram showing the separate stage cyclones for removal of catalyst fines from product effluent and the purge of stagnant zones within the reactor.

In FIG. 2 is shown reactor 2 with feed stream 1 again entering the bottom of the reactor. A purge stream 12 is shown entering the reactor at a port 13. Within the reactor is a first stage cyclone 14 to separate catalyst from the product gas. The majority of the catalyst particles within the product gas are removed by this first stage cyclone with the catalyst passing down into the lower part of the reactor and the product gas going through a line 28 to a reaction surge vessel 16 having at least one cyclonic separation means 18 for further removal of the catalyst from the product stream. The catalyst falls from the cyclone and can be stored in a catalyst hopper 20. The catalyst is shown being sent through a regeneration zone 22 and returned to the reactor through a line 24. Optionally, the catalyst may be returned directly to the reactor. These cyclones are more broadly referred to as vapor-solid cyclonic separation. The product gas is seen exiting through a line 26.

A mixture of deactivated catalyst particles and olefinic reaction products is formed in the reactor. This mixture travels up the riser section of the reaction zone and goes through a series of vapor-solid separation operations to produce a stream of deactivated catalyst particles and a conversion zone product effluent stream containing light olefins, unreacted oxygenates, $H_2O$, other reaction products and undesired amounts of contaminating catalyst particles. During the course of the highly exothermic MTO reaction that occurs in the reaction zone of the reactor, a layer of carbonaceous material coats the outer surface of the catalyst particles and this layer of carbonaceous deposits acts to deactivate the catalyst particles at least in part to the extent that at least a portion of these catalyst particles must have their activity restored in associated catalyst regeneration zone 22. The spent catalyst passes through an outlet 19 to a line 21 and then to regeneration zone 22. These carbonaceous deposits are commonly referred to as "coke" and are customarily removed by an oxidation procedure. A catalyst stream then is returned to the reaction zone. At least a portion of the deactivated catalyst material recovered from the cyclonic separation means are stripped of volatile hydrocarbons and passed via a line 23 to regeneration zone 22 wherein at least a significant portion of the carbonaceous deposits are oxidatively removed with resulting production of a stream of regenerated catalyst particles which flow via line 24 back to the reaction zone for further use in converting feed stream 1. A relatively small proportion (usually less than 1%) of the catalyst returned to the regeneration zone passes through line 24. Despite the use of one or more vapor-solid cyclonic separation means in the reaction zone to scrub the catalyst particles from the product effluent stream there is in actual practice still a significant amount of catalyst particles that are present in the product effluent stream. It has been found effective to locate further cyclonic separation means 18 for further removal of the catalyst particles from the product effluent stream. These contaminating catalyst particles can be recovered by a quench tower located upstream of the downstream compression means. The degree of contamination of the product effluent stream by these catalyst particles corresponds to about 0.01 to 0.1 mass-% of the effluent product stream and therefore represents a substantial source of continuing catalyst loss from the catalyst inventory that circulates in and through the MTO conversion zone in reactor 2 and the associated catalyst regeneration zone.

For purposes of the present invention, we prefer to use liquid-solid cyclones or hydrocyclones for this application in view of their efficiency and relatively low capital and operating costs but any other suitable liquid-solid separating means can be used for their applications if locally available.

What is claimed is:

1. A process for conversion of oxygenates to olefins, said process comprising:
    contacting within a reactor said oxygenates with a catalyst to catalytically convert said oxygenates to an effluent stream comprising light olefins wherein said reactor comprises at least two zones, a first zone wherein gas travels at a faster rate than a second zone wherein a gas travels at a slower rate; and wherein
    a purge gas comprising a quantity of inert gas is inserted into said second zone to increase circulation of any materials located in said second zone and wherein said oxygenates enter said first zone.

2. The process of claim 1 wherein said inert gas is selected from the group consisting of a mixture of methane and hydrogen, nitrogen and mixtures thereof.

3. The process of claim 2 wherein said methane and hydrogen is produced by a product separator that removes methane and hydrogen from a product stream.

4. The process of claim 1 wherein said inert gas provides an increase in mixing of reaction by-products.

5. The process of claim 1 wherein said second zone is above said first zone.

* * * * *

UNITED STATES PATENT AND TRADEMARK OFFICE
CERTIFICATE OF CORRECTION

PATENT NO. : 7,622,625 B2  Page 1 of 1
APPLICATION NO. : 11/235974
DATED : November 24, 2009
INVENTOR(S) : Palmas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 803 days.

Signed and Sealed this

Twenty-sixth Day of October, 2010

David J. Kappos
*Director of the United States Patent and Trademark Office*